United States Patent [19]
Schmied et al.

[11] Patent Number: 5,393,873
[45] Date of Patent: Feb. 28, 1995

[54] PEPTIDES WITH ANTICOAGULANT ACTIVITY

[75] Inventors: Bernhard Schmied, Frankenthal; Hans W. Hoeffken; Wilfried Hornberger, both of Ludwigshafen; Harald Bernard, Bad Duerkheim, all of Germany

[73] Assignee: BASF Aktiengesellschaft, Ludwigshafen, Germany

[21] Appl. No.: 94,084

[22] PCT Filed: Nov. 21, 1991

[86] PCT No.: PCT/EP91/02191

§ 371 Date: Jul. 29, 1993

§ 102(e) Date: Jul. 29, 1993

[87] PCT Pub. No.: WO92/13879

PCT Pub. Date: Aug. 20, 1992

[30] Foreign Application Priority Data

Feb. 7, 1991 [DE] Germany ............... 4103649

[51] Int. Cl.$^6$ ............. A61K 37/02; C07K 5/00; C07K 7/00; C07K 15/00
[52] U.S. Cl. ........................................ 530/328
[58] Field of Search .................. 514/15; 530/328

[56] References Cited

FOREIGN PATENT DOCUMENTS

| | | |
|---|---|---|
| 276014 | 7/1988 | European Pat. Off. |
| 291981 | 11/1988 | European Pat. Off. ....... C07K 7/00 |
| 372670 | 12/1988 | European Pat. Off. ..... A61K 37/64 |
| 372503 | 6/1990 | European Pat. Off. |
| 443429 | 8/1991 | European Pat. Off. ....... C07K 7/00 |
| 443598 | 8/1991 | European Pat. Off. ....... C07K 7/00 |
| WO90/03391 | 4/1990 | WIPO .............. C07K 7/06 |
| WO91/01328 | 2/1991 | WIPO .............. C07K 7/08 |

OTHER PUBLICATIONS

Marseigne et al., J. Org. Chem., vol. 53, p. 23621 (1988).
Journal of Medicinal Chemistry, vol. 31, 1988, Jan.–Jun., pp. 1009–1011.

Primary Examiner—Robert J. Hill, Jr.
Assistant Examiner—Sheela J. Huff
Attorney, Agent, or Firm—Keil & Weinkauf

[57] ABSTRACT

Peptides of the formula $$X-A^1-A^2-A^3-A^4-A^5-Glu-A^6-NH-CH(CH_2-C_6H_4-CH_2-W)-CO-A^7-Y$$

where X, $A^1$–$A^7$ Y and W have the meanings stated in the description, and the preparation thereof are described. The peptides are suitable for controlling diseases.

1 Claim, No Drawings

PEPTIDES WITH ANTICOAGULANT ACTIVITY

Hirudin is a natural substance which has anticoagulant properties and is produced in the salivary glands of the leech Hirudo medicinalis. Hirudin is a mixture of polypeptides with 64–66 amino acids. The main component of this mixture is a polypeptide which has 65 amino acids and which has O-sulfate on tyrosine 63: SEQ. NO. 1

Val-Val-Tyr-Thr-Asp-Cys-Thr-Glu-Ser-Gly-Gln-Asn-Leu-Cys-Leu-Cys-Glu-Gly-Ser-Asn-Val-Cys-Gly-Gln-Gly-Asn-Lys-Cys-Ile-Leu-Gly-Ser-Asp-Gly-Glu-Lys-Asn-Gly-Cys-Val-Thr-Gly-Glu-Gly-Thr-Pro-Lys-Pro-Gln-Ser-His-Asn-Asp-Gly-Asp-Phe-Glu-Glu-Ile-Pro-Glu-Glu-Tyr(SO$_3$H)-Leu-Gln

Hirudin binds very strongly and with high specificity to thrombin, which is the key enzyme in the coagulation cascade. The thrombin-hirudin complex is no longer able to cleave fibrinogen, the natural substrate for thrombin.

The anticoagulant action suggests that hirudin is a potential drug. However, natural (O-sulfate) hirudin can be isolated from the leeches only in very small yields and with great effort. Recombinant hirudin contains no sulfated tyrosine and has a distinctly less satisfactory binding constant for thrombin.

Hirudin intended for medical uses and isolated from cellular material must be purified with particular care. Residual DNA, foreign proteins, toxins or viral contaminations must be eliminated in all circumstances. In addition, reproducible oral or transdermal administration of a polypeptide of this size is scarcely conceivable, even using pharmaceutical aids.

For the stated reasons, early attempts were made to derive from the hirudin sequence oligopeptides which likewise have anticoagulant properties but can be prepared by complete synthesis and thus at reasonable cost and in high purity.

Many of these peptides disclosed in the literature in fact have thrombin-inhibiting properties (J. Med. Chem. 31 (1988) 1009; EP 291981). However, the potency of these compounds decreases greatly as the chain length is reduced. The EC$_{100}$ of the C-terminal decapeptide hirudin$_{56-65}$ is about 2000 times that of hirudin.

We have found that with suitable substitution it is possible for the potency of the thrombin-inhibiting action of short peptides derived from the C terminus of hirudin to reach the same order of magnitude as that of hirudin.

The present invention relates to peptides of the formula I

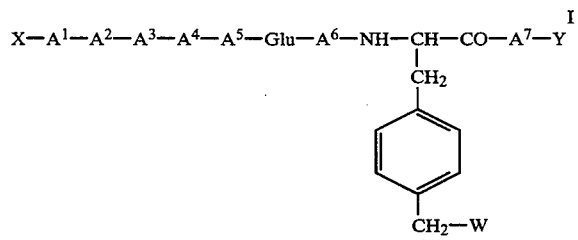

where

X is H, acetyl, succinyl, maleoyl, phthaloyl or fumaroyl,

A$^1$ is Phe, Tyr or Cha,
A$^2$ is Glu or D-Glu,
A$^3$ is Glu, Pro or Hyp,
A$^4$ is Ile, Leu, Val or Cha,
A$^5$ is Pro or Hyp,
A$^6$ is Glu or D-Glu,
A$^7$ is Leu, D-Leu, Ile, D-Ile, Cha or D-Cha,
Y is OH, Gln-OH, Gln-NH$_2$, D-Gln-OH, D-Gln-NH$_2$, Glu-OH, Glu-NH$_2$, D-Glu-OH or D-Glu-NH$_2$ and
W is SO$_3$H or PO$_3$H$_2$, and the salts thereof with physiologically tolerated bases or acids.

The conventional three-letter code is used for abbreviating the amino acids; Cha is cyclohexylalanine and Hyp is trans-4-hydroxyproline. Unless otherwise specified, the amino acids have the L configuration. The unnatural amino acids which are derived from phenylalanine and contain W can have either the L or D configuration.

In formula I, X is preferably succinyl, A$^1$ is preferably Tyr, A$^2$ is preferably Glu, A$^3$ is preferably Pro or Hyp, A$^4$ is preferably Ile, Val or Cha, A$^5$ is preferably Hyp, A$^6$ is preferably Glu, A$^7$ is preferably Leu, Ile or Cha and Y is preferably OH, Gln-OH, D-Gln-OH, Glu-OH or D-Glu-OH.

Physiologically tolerated acids which may be particularly mentioned are: hydrochloric acid, citric acid, tartaric acid, lactic acid, phosphoric acid, methanesulfonic acid, acetic acid, formic acid, maleic acid, fumaric acid, malic acid, succinic acid, malonicacid, sulfuric acid, L-glutamic acid, L-aspartic acid, pyruvic acid, mucic acid, benzoic acid, glucuronic acid, oxalic acid, ascorbic acid and acetylglycine.

Suitable physiologically tolerated bases are hydroxides and bicarbonates of the following substances: aluminum, calcium, potassium, lithium, magnesium, sodium, diethanolamine, ethylenediamine and meglumine.

The novel compounds can be prepared by methods known in peptide chemistry.

Thus, the peptides can be assembled sequentially from amino acids or by linking suitable peptide fragments. In the case of sequential assemblage, the peptide chain is extended stepwise by one amino acid each time, starting at the C terminus. In the case of fragment coupling it is possible to link together fragments of different lengths, it being possible once again for the fragments to be obtained by sequential assemblage from amino acids or in turn by fragment coupling.

In the case both of sequential assemblage and fragment coupling it is necessary for the building blocks to be linked by forming an amide linkage. Enzymatic and chemical methods are suitable for this.

Chemical methods for forming the amide linkage are dealt with in detail by Müller, Methoden der Organischen Chemie Vol XV/2, pp 1–364, Thieme Verlag, Stuttgart, 1974; Stewart, Young, Solid Phase Peptide Synthesis, pp 31–34, 71–82, Pierce Chemical Company, Rockford, 1984; Bodanszky, Klausner, Ondetti, Peptide Synthesis, pp 85–128, John Wiley & Sons, New York, 1976 and other standard works of peptide chemistry. Particularly preferred are the azide method, the symmetrical and mixed anhydride method, active esters generated in situ or preformed, and the formation of amide linkages with the aid of coupling reagents (activators), especially dicyclohexylcarbodiimide (DCC), diisopropylcarbodiimide (DIC), 1-ethoxycarbonyl-2-ethoxy-1,2-dihydroquinoline (EEDQ), 1-ethyl-3-(3- dimethylaminopropyl)carbodiimide hydrochloride ( EDCI ), n-propanephosphonic anhydride (PPA), N,N-bis(2-oxo-3-oxazolidinyl) amidophosphoryl chloride ( BOP-Cl ), diphenylphosphoryl azide, ( DPPA), Castro's reagent ( BOP ), 2-(1H-benzotriazol-1-yl )-1,1,3,3-tetramethyluronium salts (HBTU), 2,5-diphenyl-2,3-dihydro-3-oxo-4-hydroxythiophene dioxide ( Steglich's reagent; HOTDO ) and 1,1′-carbonyldiimidazole (CDI). The coupling reagents can be used alone or combined with additives such as 4-dimethylaminopyridine (DMAP), N-hydroxybenzotriazole (HOBt),N-hydroxybenzotriazine (HOOBt), N-hydroxysuccinimide (HOSu) or 2-hydroxypyridine.

Whereas it is normally possible to dispense with protective groups in enzymatic peptide synthesis, reversible protection of the reactive groups which are not involved in the formation of the amide linkage is necessary on both reactants for chemical synthesis. In the case of the claimed compounds of the formula I, the derivatized N terminus is also important since it modulates the potency.

Three conventional protective group techniques are preferred in the chemical peptide syntheses: the benzyloxycarbonyl ( Z ), the t-butyloxycarbonyl ( Boc ) and the 9-fluorenylmethyloxycarbonyl(Fmoc) protective group techniques. In each case the protective group on the α-amino of the chain-extending building block is indicated. The side-chain protective groups on the trifunctional amino acids are chosen so that they are not necessarily eliminated together with the α-amino protective group. Detailed reviews of amino acid protective groups are given by Müller, Methoden der Organischen Chemie, Vol XV/1, pp 20–906, Thieme Verlag, Stuttgart, 1974 and Bodanszky, The Practice of Peptide Synthesis, Springer-Verlag, Berlin 1984. The building blocks used to assemble the peptide chain can be reacted in solution, in suspension or by processes similar to that described by Merrifield in J. Amer. Chem. Soc. 85 (1963) 2149. Particularly preferred processes are those in which peptides are assembled sequentially or by fragment coupling using the Z, Boc or Fmoc protective group technique, in which case the reactants are reacted in solution, and processes in which, similar to the said Merrifield technique, one reactant is bonded to an insoluble polymeric support (also called resin hereinafter). In this case the peptide is typically assembled sequentially on the polymeric support, using the Boc or Fmoc protective group technique, with the growing peptide chain being covalently bonded at the C terminus to the insoluble resin particles. This procedure permits reagents and byproducts to be removed by filtration, and thus recrystallization of intermediates is unnecessary.

The protective amino acids can be bonded to any suitable polymers, which merely need to be insoluble in the solvents used and to have a stable physical form which makes filtration easy. The polymer must contain a functional group to which the first protected amino acid can be firmly linked by covalent bonding. Suitable for this purpose are a wide variety of polymers, e.g. cellulose, polyvinyl alcohol, polymethacrylate, sulfonated polystyrene, chloromethylated styrene/divinylbenzene copolymer (Merrifield resin), 4-methylbenzhydrylamineresin (MBHA-resin), phenylacetamidomethyl-resin (Pam-resin), p-benzyloxybenzyl alcohol-resin, benzhydryl-amine-resin (BHA-resin), 4-(hydroxymethyl)-benzoyloxy-methyl-resin, the resin of Breipohl et al. (Tetrahedron Lett. 28 (1987) 565; supplied by BACHEM), HYCRAM resin (supplied by ORPEGEN) or SASRIN resin (supplied by BACHEM).

Solvents suitable for peptide synthesis in solution are all those which are inert under the reaction conditions, especially water, N,N-dimethylformamide (DMF), dimethyl sulfoxide (DMSO), acetonitrile, dichloromethane (DCM), 1,4-dioxane, tetrahydrofuran (THF), N-methyl-2-pyrrolidone (NMP) and mixtures of the said solvents. Peptide synthesis on a polymeric support can be carried out in all inert organic solvents in which the amino acid derivatives used are soluble; however, preferred solvents additionally have resin-swelling properties, such as DMF, DCM, NMP, acetonitrile and DMSO and mixtures of these solvents.

After the synthesis is complete, the peptide is eliminated from the polymeric support. The conditions suitable for elimination from the various resin types are disclosed in the literature. The cleavage reactions most commonly used are acid- and palladium-catalyzed, especially cleavage in liquid anhydrous hydrogen fluoride, in anhydrous trifluoromethanesulfonic acid, in dilute or concentrated trifluoroacetic acid or palladium-catalyzed cleavage in THF or THF-DCM mixtures in the presence of a weak base such as morpholine. Depending on the choice of the protective groups, these can be retained under the cleavage conditions or likewise eliminated. Partial deprotection of the peptide may also be worthwhile, or post-synthesis derivatization of the N terminus exposed on cleavage, if the properties of the compounds benefit from this.

All the building blocks used for the peptide synthesis are commercially available, with the exception of the amino acids of the formula II (where W has the meanings indicated for formula I)

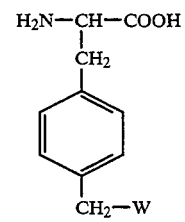

which can be obtained by acetamidomalonic ester synthesis or other methods disclosed in the literature (E. Müller, Methoden der Organischen Chemie, Vol. XI/2; 1958) for preparing amino acids.

Depending on the precursors and the reaction conditions, the resulting amino acids of the formula II either have defined stereochemistry or are racemic. The racemic amino acids of the formula II can be separated into their antipodes by methods disclosed in the literature, or the racemates are used in the peptide synthesis and the resulting diastereomeric peptide mixtures are separated.

The novel peptides were characterized as thrombin inhibitors using the following test systems:

1. Thrombin time (TT) in vitro

Citrated plasma is obtained by mixing human blood taken from an arm by venepuncture with sodium citrate (9 parts of blood +1 part of 0.11 mol/1 sodium citrate) and subsequently centrifuging at 1600 xg and room temperature for 10 min. 50 μl of citrated plasma are added to 50 μl of the substance solution or solvent and incubated at 37° C. for 2 min. Then 100 μl of thrombin reagent (Boehringer Mannheim) at 37° C. are pipetted in, and the time until coagulation starts is measured in a photometric coagulometer.

The $EC_{100}$, which is the concentration of a test substance in mol/l which increases the plasma thrombin time by 100%, is calculated as a measure of relative activity.

The plasma thrombin time embraces the thrombin-induced fibrin formation from fibrinogen and the aggregation of fibrin, i.e. the last step in coagulation.

2. Amidolytic determination of thrombin activity (similarly for other serine proteases: trypsin, chymotrypsin, plasmin, factor Xa, active protein C)

| Principle of the test: chromogenic substrate | serine protease peptide + p-nitroaniline (yellow) |
|---|---|

250 μl samples of thrombin (0.124 IU/ml, final concentration 0.1 IU/ml) in tris buffer (tris 50 mmol/l, NaCl 154 mmol/l, pH 8.0) are introduced into microtiter plates. This solution is mixed with 10 μl of solvent (control) or test substance for 1 min and incubated at 25° C. for 4 min. The reaction is then started by adding 50 μl of substrate solution (S-2238, 0.62 mmol/l, final concentration 0.1 mmol/l), briefly mixing and then incubating at 25° C. After 5 min, the reaction is stopped by adding 50 μl of 35% strength acetic acid, and the extinction at 405 nm (compared with 630 nm) is measured. The extinction measured after the reaction is complete is proportional to the enzyme activity.

The $IC_{50}$, which is the concentration of a test substance in mol/l which reduces the enzyme activity by 50%, is calculated as a measure of relative activity.

The effect on the amidolytic activity of other serine proteases

| trypsin (0.1 mg/l) | with S-2222 (0.1 mmol/l) |
| chymotrypsin (0.2 mg/l) | with S-2586 (0.1 mmol/l) |
| plasmin (0.04 CU/ml) | with S-2251 (0.1 mmol/l) |
| factor Xa (0.2 nkat/ml) | with S-2765 (0.1 mmol/l) |
| active protein C | with S-2366 (0.2 mmol/l) |

(in each case final concentration in the test) is investigated in a similar way to thrombin. The results of these tests provide information about the selectivity of the effect of test substances.

3. Thrombin-induced platelet aggregation in vitro

Fresh human citrated blood (9 parts of blood +1 part of 0.011 mol/l sodium citrate) is centrifuged to obtain platelet-rich plasma (PRP) and platelet-poor plasma (PPP) at 250 xg for 16 min and 3670 xg for 20 min respectively.

Platelet aggregation is determined by mixing 445 μl of PRP with 5 μl of solvent (control) or test substance and incubating at room temperature for 5 min. The mixture is then incubated in an aggregometer (ELVI 840) at 37° C. for 3 min and stirred at 1000 rpm for 4 min. Aggregation is started by adding 50 μl of thrombin solution (final concentration in the mixture: 0.15 IU/ml). The platelet aggregation is determined from the change in the measured transmission per unit time in the sample (slope method).

The $IC_{50}$, which is the concentration of a test substance in mol/l which inhibits platelet aggregation by 50%, is calculated as a measure of relative activity.

4. Antithrombotic effect in the arteriovenous shunt in the rat

In this experiment, a glass capillary in an arteriovenous shunt acts as thrombogenic surface and induces thrombosis.

The anesthetized (urethane 25%, 2×8 mg/kg i.p.) rat is fixed in the dorsal position on a stage maintained at 37° C. The right carotid artery and jugular vein are exposed and short polyethylene catheters (Portex, PE 50) are implanted, filled with physiological saline and clamped. The free ends of the catheters are connected by a 20 mm-long glass capillary (internal diameter 1.0 mm) which acts as thrombogenic surface.

The test substance can be administered i.v., s.c., orally or by infusion. After the required incubation time (5, 60 or 360 min) with the test substance or solvent (control) the shunt is opened by removing the clamps. The blood flow through the shunt leads to a rapid rise in the shunt temperature, which is measured at the middle of the glass capillary. The increase from room temperature to body temperature is an indicator of the patency of the shunt. The temperature is recorded continuously until the shunt is occluded, but for not more than 30 min.

In addition, when the shunt is opened and at the end of the experiment, blood samples are taken for determination of the anti-FIIa activity in the plasma.

The experiment is evaluated quantitatively by linear regression calculation on the log dose and the time (difference between the occlusion times in the treated group and control group). The activities of different test substances are compared by calculating the ED15min (the dose which increases the occlusion time from that in the control group by 15 min) from the equation of the regression lines.

The novel compounds can be prepared straightforwardly and in high yield, are chemically stable, have no immunogenic potential and are suitable for the treatment and prophylaxis of thromboembolic disorders such as myocardial infarct, peripheral arterial occlusive disease, deep vein thromboses, pulmonary embolism and for preventing reocclusion after restoration of patency to arteries and veins. They are furthermore suitable for coating artificial surfaces which come into contact with blood or plasma (e.g. dialysis membranes).

The novel compounds have higher activities than previously described peptides which are likewise derived from hirudin, such as MD 28050 (Thrombosis and Haemostasis 63 (1990) 208-214; EP 0 372 503), Hirulog-1 (Biochemistry 29 (1990) 7095-7101; WO 91/02750) and P79 (FEBS Letters 282 (1991) 47-52). The peptides synthesized using the unnatural amino acid of the formula II where W is $SO_3H$ are considerably more active than peptides whose sequence is otherwise similar but which use the unnatural amino acid

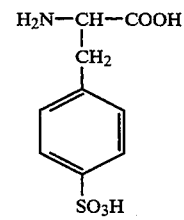

This amino acid has been used in other peptides derived from hirudin (EP 0 443 598). The potency of these novel compounds is of the same order of magnitude as that of recombinant hirudin.

EXAMPLES

1. Synthesis of the amino acids of the formula II

The unnatural amino acids of the formula II were prepared by a synthesis described in the literature (J. Org. chem. 53 (1988) 3621–3624; EP 0 354 108).

2. Synthesis of the peptides of the formula I 2.1. General method

The peptides of the formula I were synthesized by standard methods of solid-phase peptide synthesis in a semiautomatic LABORTEC model SP650 peptide synthesizer. The ratios of amounts and volumes of the reagents were those specified in the user manual, unless otherwise indicated. Each coupling and elimination step was checked for completeness and repeated if necessary.

2.1.1 Typical synthetic cycle for the Boc protective group technique:

| | | |
|---|---|---|
| 1. trifluoroacetic acid and anisole in DCM (480:20:500) | 1 × | 5 min |
| 2. as 1. | 1 × | 15 min |
| 3. washing with DCM | 3 × | 5 min |
| 4. diisopropylamine in DCM (100:900) | 3 × | 3 min |
| 5. washing with DCM | 3 × | 5 min |
| 6. coupling: 1.5 eq amino acid, 1.5 eq of 0.5 M TBTU in DMF, 1.5 eq of 0.5 M diisopropylethylamine in DCM | 1 × | 3 min |
| 7. washing with DCM | 3 × | 5 min |
| 8. if conversion is incomplete, repetition of coupling (ie. back to 6.) or capping. | | |
| 9. back to 1. | | |

2.1.2 Typical synthetic cycle for the Fmoc protective group technique

| | | |
|---|---|---|
| 1. piperidine in DMF (200:800) | 1 × | 5 min |
| 2. as 1. | 1 × | 15 min |
| 3. washing with DMF | 2 × | 5 min |
| 4. washing with DCM | 2 × | 5 min |
| 5. coupling as described in 2.1.1. | 1 × | 10 min |
| 6. washing with DCM | 2 × | 5 min |
| 7. washing with DMF | 2 × | 5 min |
| 8. if conversion is incomplete, repetition of the coupling (ie. back to 5.) or capping | | |
| 9. back to 1. | | |

2.1.3 Workup of the peptide-resins obtained in 2.1.1.

The peptide-resin obtained in 2.1.1 was dried under reduced pressure and transferred into a reaction vessel in a TEFLON HF apparatus (supplied by PENINSULA). After addition of a scavenger, preferably anisole (1 ml/g of resin), hydrogen fluoride (10 ml/g of resin) was condensed in while cooling with liquid $N_2$. The mixture was allowed to warm to 0° C. and stirred at this temperature for 45 min. The hydrogen fluoride was then stripped off under reduced pressure, and the residue was washed with ethyl acetate to remove remaining scavenger. The peptide was extracted with 30% strength acetic acid, the extract was filtered and the filtrate was lyophilized.

2.1.4 Workup of the peptide-resins obtained in 2.1.2

The peptide-resin obtained as in 2.1.2. was dried under reduced pressure and subsequently subjected to one of the following cleavage procedures depending on the amino-acid composition (Wade, Tregear, Howard Florey Fmoc-Workshop Manual, Melbourne 1985).

| The peptide contained | | | Cleavage conditions | | | |
|---|---|---|---|---|---|---|
| Arg(Mtr) | Met | Trp | TFA | | Scavenger | Reaction time |
| no | no | no | 95% | 5% | $H_2$ | 1.5 h |
| yes | no | no | 95% | 5% | thioanisole | 3 h |
| no | yes | no | 95% | 5% | ethyl methyl sulfide | 1.5 h |
| no | no | yes | 95% | 5% | ethanedithiol/anisole (1:3) | 1.5 h |
| no | yes | yes | 95% | 5% | ethanedithiol/anisole/ ethyl methyl sulfide (1:3:1) | 1.5 h |
| yes | yes | yes | 93% | 7% | ethanedithiol/anisole/ ethyl methyl sulfide (1:3:3) | 3 h |

The suspension of the peptide-resin in the suitable TFA mixture was stirred at room temperature for the stated time, and then the resin was filtered off and washed with TFA and DCM. The filtrate and the washings were concentrated and the peptide was precipitated by adding diethyl ether. After cooling in an ice bath, the precipitate was filtered off, taken up in 30% acetic acid and lyophilized.

2.1.5 Purification and characterization of the peptides

The quality of the crude peptides and of the purified peptides was assessed by HPLC; the purification was carried out by MPLC or by a combination of gel chromatography and MPLC.

HPLC:

Apparatus: HP 1090 liquid chromatograph

Stationary Phase: 100×2.1 mm VYDAC C18 (TPB 218); 5 μm; 300 Å

Mobile Phase: (A) 0.1% TFA in $H_2O$; (B) 0.1% TFA in $CH_3CN$;

Flow rate: 0.2 ml/min; temp. 40° C.

Gradients:
 (a): from 0% (B) at 0.5% $min^{-1}$
 (b): from 5% (B) at 1.0% $min^{-1}$
 (c): from 35% (B) at 1.0% $min^{-1}$ Sample injected: 3 μl about 0.03% strength solution in the eluent Detection: 205 nm

MPLC:

Apparatus: Labomatic gradient medium pressure chromatography station

Stationary Phase: 26×450 mm to 37×450 mm Eurosil Bioselect 100/30 C 18; 20–45 μm; 100 Å

Mobile Phase: (A) 0.1% TFA in $H_2O$; (B) CH3CN

Gradient: step gradient at 0.25% $min^{31\ 1}$ during elution

Detection: 205 to 220 nm

Gel chromatography:

Stationary phases: SEPHADEX ® G-10 and -LH20

Mobile Phases: 10% AcOH and MeOH

Detection: UV and RI detectors in series.

The purified peptides were characterized by amino-acid analysis (AAA), fast atom bombardment mass spectrometry (AB-MS) and, occasionally, sequencing (SQ) or NMR spectroscopy (NMR).

2.2 Specific methods 2.2.1 [p-Sulfo-Phe$^{63}$]-N$^\alpha$-acetyl-hirudin$_{56-65}$ 1.00 g (0.47 meq) of Boc-Gln-Pam-resin was reacted as in 2.1.1 with:

| | |
|---|---|
| Boc—Leu—OH | Boc—Ile—OH |
| Boc—(p-sulfo)Phe—OH | Boc—Glu(OChx)—OH |
| Boc—Glu(OChx)—OH | Boc—Glu(OChx)—OH |
| Boc—Glu(OChx)—OH | Boc—Phe—OH |
| Boc—Pro—OH | |

After N-acetylation with acetic anhydride, workup as in 2.1.3 gave a crude yield of 305 mg of lyophilizate.

The crude peptide was purified by MPLC as in 2.1.5. HPLC retention time (gradient b): 19.5 min; AAA: correct; FAB-MS: 1402

2.2.2 [D-p-Sulfomethyl-Phe$^{63}$]-N$^\alpha$-acetyl-hirudin$_{56-65}$ and [L-p-sulfomethyl-Phe$^{63}$]-N$^\alpha$-acetyl-hirudin$_{56-65}$ 2.0 g (1.54 meq) of Boc-Gln-Pam-resin were reacted as in 2.1.1 with:

| | |
|---|---|
| Boc—Leu—OH | Boc—Ile—OH |
| Boc—D,L-(p-sulfomethyl)Phe—OH | Boc—Glu(OChx)—OH |
| Boc—Glu(OChx)—OH | Boc—Glu(OChx)—OH |
| Boc—Glu(OChx)—OH | Boc—Phe—OH |
| Boc—Pro—OH | |

After N-acetylation with acetic anhydride, workup as in 2.1.3 gave a crude yield of 304 mg of lyophilizate.

The crude peptide was purified by MPLC as in 2.1.5, it being possible to separate the two diastereomers.

HPLC retention times (gradient b): 18.5 and 19.5 min; AAA: correct; FAB-MS: 1416 and 1416

[D-p-Phosphonomethyl-Phe$^{63}$]-N$^\alpha$-acetyl-hirudin$_{56-65}$ and [L-p-phosphonomethyl-Phe$^{63}$]-N$^\alpha$-acetyl-hirudin$_{56-65}$ were prepared similarly [HPLC retention times (gradient b): 19.5 and 21.0 min; AAA: correct; FAB-MS: 1418 and 1418].

2.2.3 [D-p-Sulfomethyl-Phe$^{63}$]-N$^\alpha$-succinyl-hirudin$_{56-65}$ and [L-p-sulfomethyl-Phe$^{63}$]-N$^\alpha$-succinyl-hirudin$_{56-65}$ 2.0 g (1.54 meq) of Boc-Gln-Pam-resin were reacted as in 2.1.1 with:

| | |
|---|---|
| Boc—Leu—OH | Boc—Ile—OH |
| Boc—D,L-(p-sulfomethyl)Phe—OH | Boc—Glu(OChx)—OH |
| Boc—Glu(OChx)—OH | Boc—Glu(OChx)—OH |
| Boc—Glu(OChx)—OH | Boc—Phe—OH |
| Boc—Pro—OH | |

After N-succinylation with succinic anhydride, workup as in 2.1.3 gave a crude yield of 364 mg of lyophilizate.

The crude peptide was purified by MPLC as in 2.1.5.

HPLC retention time (gradient b): 18.5 min and 20.0 min; AAA: correct; FAB-MS: 1474 and 1474

The following were prepared in a similar way: [p-Sulfo-Phe$^{63}$]-N$^\alpha$-succinyl-hirudin$_{56-65}$ HPLC retention time (gradient b): 23.0 min; AAA: correct; FAB-MS: 1460

[Hyp$^{60}$,p-Sulfo-Phe$^{63}$]-N$^\alpha$-succinyl-hirudin$_{56-65}$
HPLC retention time (gradient b): 20.0 min; AAA: correct; FAB-MS: 1476

[Hyp$^{60}$,p-Sulfo-Phe$^{63}$,Cha$^{64}$]-N$^\alpha$-succinyl-hirudin$_{56-65}$ HPLC retention time (gradient b): 25.0 min; AAA: correct; FAB-MS: 1516

[Tyr$^{56}$,D-p-Sulfomethyl-Phe$^{63}$,Cha$^{64}$]-N$^\alpha$-succinyl-hirudin$_{56-65}$ and
[Tyr$^{56}$,L-p-sulfomethyl-Phe$^{63}$,Cha$^{64}$]-N$^\alpha$-succinyl-hirudin$_{56-65}$ HPLC retention time (gradient b): 23.0 min and 26.5 min; AAA: correct; FAB-MS: 1530 and 1530

[Tyr$^{56}$,Pro$^{58}$,D-p Sulfomethyl-Phe$^{63}$,Cha$^{64}$]-N$^\alpha$-succinyl-hirudin$_{56-65}$ and
[Tyr$^{56}$,Pro$^{58}$,L-p-sulfomethyl-phe$^{63}$,Cha$^{64}$-N$^\alpha$-succinyl-hirudin$_{56-65}$ HPLC retention time (gradient b): 18.0 min and 19.5 min; AAA: correct; FAB-MS: 1498 and 1498

[Tyr$^{56}$,Pro$^{58}$,Hyp$^{60}$,D-p-Sulfomethyl-Phe$^{63}$,Cha$^{64}$]-N$^\alpha$-succinyl-hirudin$_{56-65}$ and Tyr$^{56}$,Pro$^{58}$,Hyp$^{60}$,L-p-sulfomethyl-Phe$^{63}$,Cha$^{64}$]-N$^\alpha$-succinyl-hirudin$_{56-65}$
HPLC retention time (gradient b): 19.0 min and 20.0 min; AAA: correct; FAB-MS: 1514 and 1514

[Tyr$^{56}$,Pro$^{58}$,Hyp$^{60}$,D-p-Sulfomethyl-Phe$^{63}$,Cha$^{64}$,Glu$^{65}$]-N$^\alpha$-succinyl-hirudin$_{56-65}$ and [Tyr$^{56}$,Pro$^{58}$,Hyp$^{60}$,L-p-sulfomethyl-Phe$^{63}$,Cha$^{64}$,Glu$^{65}$]-N$^\alpha$-succinyl-hirudin$_{56-65}$ HPLC retention time (gradient b): 20.0 min and 23.0 min; AAA: correct; FAB-MS: 1515 and 1515

When racemates of the amino acids of the formula II were used in the peptide synthesis, the resulting mixtures of diastereomeric peptides were separated by MPLC. As a rule, the diastereomer with the longer HPLC retention time had a potency which was about two orders of magnitude greater than that of the diastereomer with the shorter HPLC retention time. It has not yet been possible to make an assignment concerning the enantiomers of the unnatural amino acid of the formula II present in each case.

2.3 Other examples of peptides of the formula I

The following peptides of the formula I can be synthesized as described in 2.2:

[D-p-Sulfomethyl-Phe63,Cha$^{60}$]-N$^\alpha$-succinyl-hirudin$_{56-65}$

[L-p-Sulfomethyl-Phe$^{63}$,Cha$^{60}$]-N$^\alpha$-succinyl-hirudin$_{56-65}$

[Hyp$^{60}$,D-p-Sulfomethyl-Phe$^{63}$]-N$^\alpha$-succinyl-hirudin$_{56-65}$

[Hyp$^{60}$,L-p-Sulfomethyl-Phe$^{63}$]-N$^\alpha$-succinyl-hirudin$_{56-65}$

[Hyp$^{60}$,D-p-Sulfomethyl-Phe$^{63}$,Cha$^{64}$]-N$^\alpha$-succinyl-hirudin$_{56-65}$

[Hyp$^{60}$,L-p-Sulfomethyl-Phe$^{63}$,Cha$^{64}$]-N$^\alpha$-succinyl hirudin$_{56-65}$

[Tyr$^{56}$,Hyp$^{60}$,D-p-Sulfomethyl-Phe$^{63}$,Cha$^{64}$]-N$^\alpha$-succinyl-hirudin$_{56-65}$

[Tyr$^{56}$,Hyp$^{60}$,L-p-Sulfomethyl-Phe$^{63}$,Cha$^{64}$]-N$^\alpha$-succinyl hirudin$_{56-65}$

[Tyr$^{56}$,Hyp$^{58}$,Hyp$^{60}$,D-p-Sulfomethyl-Phe$^{63}$,Cha$^{64}$]-N$^\alpha$-succinyl-hirudin$_{56-65}$

[Tyr$^{56}$,Hyp$^{58}$,Hyp$^{60}$,L-p-Sulfomethyl-Phe$^{63}$,Cha$^{64}$]-N$^\alpha$-succinyl-huridin$_{56-65}$

[Tyr$^{56}$,Pro$^{58}$,Val$^{59}$,Hyp$^{60}$,D-p-Sulfomethyl-Phe$^{63}$,Cha$^{64}$]-N$^\alpha$-succinyl-hirudin$_{56-65}$

[Tyr$^{56}$,Pro$^{58}$,Val$^{59}$,Hyp$^{60}$,L-p-Sulfomethyl-Phe$^{63}$,Cha$^{64}$]-N$^\alpha$-succinyl-hirudin$_{56-65}$

[Tyr$^{56}$,Pro$^{58}$,Cha$^{59}$,Hyp$^{60}$,D-p-Sulfomethyl-Phe$^{63}$,Ile$^{64}$]-N$^\alpha$-succinyl-hirudin$_{56-65}$

[Tyr$^{56}$,Pro$^{58}$,Cha$_{59}$,Hyp$^{60}$,L-p-Sulfomethyl-Phe$^{63}$,Ile$^{64}$]-N$^\alpha$succinyl-hirudin$_{56-65}$

[Tyr$^{56}$,Pro$^{58}$,Hyp$^{60}$,D-p-Sulfomethyl-Phe$^{63}$,Cha$_{64}$]-N$^\alpha$-succinyl-hirudin$_{56-64}$

[Tyr$^{56}$,Pro$^{58}$,Hyp$^{60}$,L-p-Sulfomethyl-Phe$^{63}$,Cha$_{64}$]-N$^{60}$ succinyl-hirudin$_{56-64}$

[Tyr$^{56}$,Pro$^{58}$,Hyp$^{60}$,D-p-Sulfomethyl-Phe$^{63}$,Cha$^{64}$D-Gln$^{65}$]-N$^\alpha$-succinyl-hirudin$_{56-65}$

[Tyr$^{56}$,Pro$^{58}$,Hyp$^{60}$,L-p-Sulfomethyl-Phe$^{63}$,Cha$^{64}$,D-Gln$^{65}$]-N$^\alpha$-Succinyl-hirudin$_{56-65}$
[Tyr$^{56}$,Pro$^{58}$,Hyp$^{60}$,D-p-Sulfomethyl-Phe$^{63}$,Cha$^{64}$,D-Glu$^{65}$]-N$^{60}$-succinyl-hirudin$_{56-65}$
[Tyr$^{56}$,Pro$^{58}$,Hyp$^{60}$,L-p-Sulfomethyl-Phe$^{63}$,Cha$^{64}$,D-Gu$^{65}$]-N$^\alpha$-Succinyl-hirudin$_{56-65}$
[Tyr$^{56}$,Hyp$^{58}$,Val$^{59}$,Hyp$^{60}$,D-p-Sulfomethyl-Phe$^{63}$,Cha$^{64}$]-N$^\alpha$]-succinyl-hirudin$_{56-65}$
[Tyr$^{56}$,Hyp$^{58}$,Val$^{59}$,Hyp$^{60}$,L-p-Sulfomethyl-Phe$^{63}$,Cha$^{64}$]-N$^\alpha$-succinyl-hirudin$_{56-65}$
[Tyr$^{56}$,Hyp$^{58}$,Cha$^{59}$,Hyp$^{60}$,D-p-Sulfomethyl-Phe$^{63}$,Ile$^{64}$]-N$^\alpha$-succinyl-hirudin$_{56-65}$
[Tyr$^{56}$,Hyp$^{58}$,Cha$^{59}$,Hyp$^{60}$,L-p-Sulfomethyl-Phe$^{63}$,Ile$^{6}$]-N$^\alpha$-succinyl-hirudin$_{56-65}$
[D-p-Phosphonomethyl-Phe$^{63}$]-N$^\alpha$-succinyl-hirudin$_{56-65}$
[L-p-Phosphonomethyl-Phe$^{63}$]-N$^\alpha$-succinyl-hirudin$_{56-65}$
[D-p-Phosphonomethyl-Phe$^{63}$,Cha$^{64}$]-N$^\alpha$-succinyl-hirudin$_{56-65}$
[L-p-Phosphonomethyl-Phe$^{63}$,Cha$^{64}$]-N$^\alpha$-succinyl-hirudin$_{56-65}$
[Tyr$^{56}$,D-p-Phosphonomethyl-Phe$^{63}$,Cha$^{64}$]-N$^\alpha$-succinyl-hirudin$_{56-65}$
[Tyr$^{56}$,L-p-Phosphonomethyl-Phe$^{63}$,Cha$^{64}$]-N$^\alpha$-succinyl-hirudin$_{56-65}$
[Tyr$^{56}$,Pro$^{58}$,D-p-Phosphonomethyl-Phe$^{63}$,Cha$^{64}$]-N$^\alpha$-succinyl-hirudin$_{56-65}$
[Tyr$^{56}$,Pro$^{58}$,L-p-Phosphonomethyl-Phe$^{63}$,Cha$^{64}$]-N$^\alpha$-succinyl-hirudin$_{56-65}$
[Hyp$^{60}$,D-p-Phosphonomethyl-Phe$^{63}$]-N$^\alpha$-succinyl-hirudin$_{56-65}$
[Hyp$^{60}$,L-p-Phosphonomethyl-Phe$^{63}$]-N$^\alpha$-succinyl-hirudin$_{56-65}$
[Hyp$^{60}$,D-p-Phosphonomethyl-Phe$^{63}$,Cha$^{64}$]-N$^\alpha$-succinyl-hirudin$_{56-65}$
[Hyp$^{60}$,L-p-Phosphonomethyl-Phe$^{63}$,Cha$^{64}$]-N$^\alpha$-succinyl-hirudin$_{56-65}$
[Tyr$^{56}$,Hyp$^{60}$,D-p-Phosphonomethyl-Phe$^{63}$,Cha$^{64}$]-N$^\alpha$-succinyl-hirudin$_{56-65}$
[Tyr$^{56}$,Hyp$^{60}$,L-p-Phosphonomethyl-Phe$^{63}$,Cha$^{64}$]-N$^\alpha$-succinyl-hirudin$_{56-65}$
[Tyr$^{56}$,Pro$^{58}$,Hyp$^{60}$,D-p-Phosphonomethyl-Phe$^{63}$,Cha$^{64}$]-N$^\alpha$-succinyl-hirudin$_{56-65}$
[Tyr$^{56}$,Pro$^{58}$,Hyp$^{60}$,L-p-Phosphonomethyl-Phe$^{63}$,Cha$^{64}$]-N$^\alpha$-succinyl-hirudin$_{56-65}$
[Tyr$^{56}$,Hyp$^{58}$,Hyp$^{60}$,D-p-Phosphonomethyl-Phe$^{63}$,Cha$^{64}$]-N$^\alpha$-succinyl-hirudin$_{56-65}$
[Tyr$^{56}$,Hyp$^{58}$,Hyp$^{60}$,L-p-Phosphonomethyl-Phe$^{63}$,Cha$^{64}$]-N$^\alpha$-succinyl-hirudin$_{56-65}$
[Tyr$^{56}$,Pro$^{58}$,Val$^{59}$,Hyp$^{60}$,D-p-Phosphonomethyl-Phe$^{63}$,Cha$^{64}$]-N$^\alpha$-succinyl-hirudin$_{56-65}$
[Tyr$^{56}$,Pro$^{58}$,Val$^{59}$,Hyp$^{60}$,L-p-Phosphonomethyl-Phe$^{63}$,Cha$^{64}$]-N$^\alpha$-succinyl-hirudin$_{56-65}$
[Tyr$^{56}$,Pro$^{58}$,Cha$^{59}$,Hyp$^{60}$,D-p-Phosphonomethyl-Phe$^{63}$,Ile$^{64}$]-N$^\alpha$-succinyl-hirudin$_{56-65}$
[Tyr$^{56}$,Pro$^{58}$,Cha$^{59}$,Hyp$^{60}$,L-p-Phosphonomethyl-Phe$^{63}$,Ile$^{64}$]-N$^\alpha$-succinyl-hirudin$_{56-65}$
[Tyr$^{56}$,Pro$^{58}$,Hyp$^{60}$,D-p-Phosphonomethyl-Phe$^{63}$,Cha$^{64}$]-N$^\alpha$-succinyl-hirudin$_{56-64}$
[Tyr$^{56}$,Pro$^{58}$,Hyp$^{60}$,L-p-Phosphonomethyl-Phe$^{63}$,Cha$^{64}$]-N$^\alpha$-succinyl-hirudin$_{56-64}$
[Tyr$^{56}$,Pro$^{58}$,Hyp$^{60}$,D-p-Phosphonomethyl-Phe$^{63}$,Cha$^{64}$, D-Gln$^{65}$]-N$^\alpha$-succinyl-hirudin$_{56-65}$
[Tyr$^{56}$,Pro$^{58}$,Hyp$^{60}$,L-p-Phosphonomethyl-Phe$^{63}$,Cha$^{64}$, D-Gln$^{65}$]-N$^\alpha$-Succinyl-hirudin$_{56-65}$
[Tyr$^{56}$,Pro$^{58}$,Hyp$^{60}$,D-p-Phosphonomethyl-Phe$^{63}$,Cha$^{64}$, Glu$^{65}$]-N$^\alpha$-succinyl-hirudin$_{56-65}$
[Tyr$^{56}$,Pro$^{58}$,Hyp$^{60}$,L-p-Phosphonomethyl-Phe$^{63}$,Cha$^{64}$Glu$^{65}$]-N$^\alpha$-succinyl-hirudin$_{56-65}$
[Tyr$^{56}$,Pro$^{58}$,Hyp$^{60}$,D-p-Phosphonomethyl-Phe$^{63}$,Cha$^{64}$, D-Glu$^{65}$]-N$^\alpha$-succinyl-hirudin$_{56-65}$
[Tyr$^{56}$,Pro$^{58}$,Hyp$^{60}$,L-p-Phosphonomethyl-Phe$^{63}$,Cha$^{64}$, D-Glu$^{65}$]-N$^\alpha$-succinyl-hirudin$_{56-65}$
[Tyr$^{56}$,Hyp$^{58}$,Val$^{59}$,Hyp$^{60}$,D-p-Phosphonomethyl-Phe$^{63}$,Cha$^{64}$]-N$^\alpha$-succinyl-hirudin$_{56-65}$
[Tyr$^{56}$,Hyp$^{58}$,Val$^{59}$,Hyp$^{60}$,L-p-Phosphonomethyl-Phe$^{63}$,Cha$^{64}$]-N$^\alpha$-succinyl-hirudin$_{56-65}$
[Tyr$^{56}$,Hyp$^{58}$,Cha$^{59}$,Hyp$^{60}$,D-p-Phosphonomethyl-Phe$^{63}$,Ile$^{64}$]-N$^\alpha$-succinyl-hirudin$_{56-65}$
[Tyr$^{56}$,Hyp$^{58}$,Cha$^{59}$,Hyp$^{60}$,L-p-Phosphonomethyl-Phe$^{63}$,Ile$^{64}$]-N$^\alpha$-succinyl-hirudin$_{56-65}$

---

We claim:
1. A peptide of the formula I
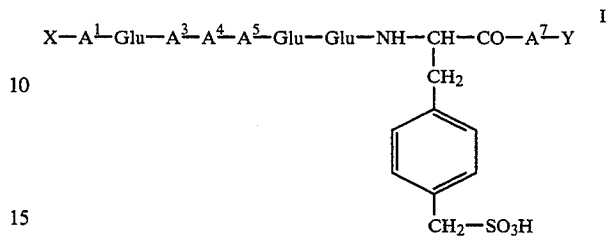
where
X is succinyl
$A^1$ is Phe or Tyr,
$A^3$ is Glu, Pro or Hyp,
$A^4$ is Ile or Cha,
$A^5$ is Pro or Hyp,
$A^7$ is Leu or Cha, and
Y is Gln-OH or Glu-OH
and the salts thereof with pharmaceutically acceptable bases or acids.
* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 65 amino acids
( B ) TYPE: amino acid
( D ) TOPOLOGY: linear ( x i ) SEQUENCE DESCRIPTION: SEQ ID NO: 1:

| Val | Val | Tyr | Thr | Asp | Cys | Thr | Glu | Ser | Gly | Gln | Asn | Leu | Cys | Leu | Cys |
|---|---|---|---|---|---|---|---|---|---|---|---|---|---|---|---|
| 1 | | | | 5 | | | | | 10 | | | | | 15 | |

| Glu | Gly | Ser | Asn | Val | Cys | Gly | Gln | Gly | Asn | Lys | Cys | Ile | Leu | Gly | Ser |
|---|---|---|---|---|---|---|---|---|---|---|---|---|---|---|---|
| | | | 20 | | | | 25 | | | | | 30 | | | |

| Asp | Gly | Glu | Lys | Asn | Gly | Cys | Val | Thr | Gly | Glu | Gly | Thr | Pro | Lys | Pro |
|---|---|---|---|---|---|---|---|---|---|---|---|---|---|---|---|
| | | 35 | | | | | 40 | | | | | 45 | | | |

| Gln | Ser | His | Asn | Asp | Gly | Asp | Phe | Glu | Glu | Ile | Pro | Glu | Glu | Xaa | Leu |
|---|---|---|---|---|---|---|---|---|---|---|---|---|---|---|---|
| | 50 | | | | 55 | | | | | 60 | | | | | |